(12) United States Patent
Ignatchenko et al.

(10) Patent No.: US 7,659,432 B2
(45) Date of Patent: Feb. 9, 2010

(54) CATALYSTS SELECTIVE FOR THE PREPARATION OF MIXED KETONES FROM A MIXTURE OF CARBOXYLIC ACIDS

(75) Inventors: Alexey V. Ignatchenko, Longview, TX (US); Michelle Manichanh King, Greeley, CO (US); Zhufang Liu, Kingsport, TN (US); Calvin W. Whiddon, Beaumont, TX (US)

(73) Assignee: Eastman Chemical Company, Kingsport, TN (US)

( * ) Notice: Subject to any disclaimer, the term of this patent is extended or adjusted under 35 U.S.C. 154(b) by 31 days.

(21) Appl. No.: 12/166,091

(22) Filed: Jul. 1, 2008

(65) Prior Publication Data

US 2009/0182173 A1 Jul. 16, 2009

Related U.S. Application Data

(62) Division of application No. 11/525,104, filed on Sep. 22, 2006, now Pat. No. 7,452,841.

(60) Provisional application No. 60/719,871, filed on Sep. 23, 2005.

(51) Int. Cl.
C07C 45/48 (2006.01)
B01J 21/00 (2006.01)
B01J 23/00 (2006.01)

(52) U.S. Cl. ................ 568/397; 502/242; 502/250; 502/349; 502/350

(58) Field of Classification Search ................ 502/242, 502/250, 349, 350; 568/397
See application file for complete search history.

(56) References Cited

U.S. PATENT DOCUMENTS

| | | | |
|---|---|---|---|
| 2,549,508 A | 4/1951 | Mottern | |
| 3,466,334 A | 9/1969 | Young et al. | |
| 3,944,622 A | 3/1976 | Okamoto et al. | |
| 3,966,822 A | 6/1976 | Fukui et al. | |
| 4,085,121 A | 4/1978 | Milberger et al. | |
| 4,307,247 A * | 12/1981 | Shaw et al. | 562/599 |
| 4,314,075 A * | 2/1982 | Shaw et al. | 562/599 |
| 4,754,674 A * | 7/1988 | Perlman | 83/422 |
| 4,806,517 A | 2/1989 | Vanderpool et al. | |
| 4,950,763 A | 8/1990 | Schommer et al. | |
| 5,001,273 A | 3/1991 | Kleine-Homann | |
| 5,204,308 A | 4/1993 | Lee et al. | |
| 5,472,924 A | 12/1995 | Afanasiev et al. | |
| 5,750,795 A * | 5/1998 | Saito | 568/397 |
| 5,902,873 A | 5/1999 | Banach et al. | |
| 6,043,189 A | 3/2000 | Narbeshuber | |
| 6,043,335 A | 3/2000 | Banach et al. | |
| 6,265,618 B1 * | 7/2001 | Zoeller et al. | 568/397 |
| 6,369,276 B1 | 4/2002 | Warren | |
| 6,391,276 B1 | 5/2002 | Suda et al. | |
| 6,392,099 B1 | 5/2002 | Warren | |
| 6,429,339 B1 * | 8/2002 | Liang et al. | 568/355 |
| 6,511,642 B1 | 1/2003 | Hatanaka et al. | |
| 6,517,629 B2 | 2/2003 | Kinniard | |
| 6,545,185 B1 | 4/2003 | Warren et al. | |
| 6,660,686 B2 | 12/2003 | Inagaki et al. | |
| 6,670,303 B1 | 12/2003 | Heineke | |
| 6,984,761 B2 * | 1/2006 | Levin et al. | 568/385 |
| 7,252,767 B2 | 8/2007 | Bortun et al. | |
| 2002/0052291 A1 | 5/2002 | Siriwardane | |
| 2002/0086795 A1 | 7/2002 | LaBarge et al. | |
| 2007/0088180 A1 | 4/2007 | Ignatchenko et al. | |
| 2007/0088181 A1 | 4/2007 | Ignatchenko et al. | |
| 2007/0100166 A1 | 5/2007 | Beavers et al. | |

FOREIGN PATENT DOCUMENTS

| | | |
|---|---|---|
| EP | 0 085 996 | 8/1983 |
| EP | 0 561 614 A2 | 9/1993 |
| EP | 1 219 351 A1 | 7/2002 |
| GB | 1417220 | 12/1975 |
| WO | 91/15462 A1 | 10/1991 |
| WO | 93/24576 A1 | 12/1993 |
| WO | 2004/016352 A1 | 2/2004 |

OTHER PUBLICATIONS

Hadjiivanov, K.I., et al., "Study of Phosphate-Modified TiO2 (Anatase)," Journal of Catalysis, 1989, pp. 498-505, vol. 116, Academic Press, Inc., Burlington, MA, USA.

Parida, K., et al., "Catalytic ketonisation of acetic acid over modified zirconia 1. Effect of alkali-metal cations as promoter," Journal of Molecular Catalysis A: Chemical, 1999, pp. 73-80, vol. 139, Elsevier Science B.V., The Netherlands.

Arpe et al., "Improved Catalyst for Ketone Synthesis from Carboxylic Acids," Brennstoff-Chemie, 48(3), 1967, pp. 69-73.

* cited by examiner

*Primary Examiner*—Cam N Nguyen
(74) *Attorney, Agent, or Firm*—William K. McGreevey; Bernard J. Graves, Jr.

(57) ABSTRACT

Mixed ketones are prepared from a mixture of carboxylic acids in a process with high selectivity by using an improved catalyst. The catalyst contains zirconium dioxide or zirconium dioxide and titanium dioxide, and a Group 1 or 2 metal silicate or phosphate salt. The new catalyst is more selective toward the formation of the mixed ketone, as opposed to a symmetrical ketone.

27 Claims, No Drawings

CATALYSTS SELECTIVE FOR THE PREPARATION OF MIXED KETONES FROM A MIXTURE OF CARBOXYLIC ACIDS

CROSS-REFERENCE TO RELATED APPLICATIONS

This application is a divisional of application Ser. No. 11/525,104, filed Sep. 22, 2006, which is U.S. Pat. No. 7,452, 841, issued on Nov. 18, 2008, which claims the benefit of the filing date of U.S. Provisional Patent Application No. 60/719, 871, filed Sep. 23, 2005; the retire content of which is hereby incorporated by reference.

FIELD OF THE INVENTION

The present invention relates to novel catalyst compositions containing zirconium dioxide or a mixture of zirconium dioxide and titanium dioxide, and a salt containing a cation selected from Groups 1 and 2 of the Periodic Table of Elements and an anion selected from silicate and phosphate. The invention also relates to processes for preparing a mixed ketone using the novel catalyst compositions.

BACKGROUND OF THE INVENTION

Ketones are useful organic solvents for painting, agricultural, and other industries. Preparation of ketones from carboxylic acids with metal oxide catalysts at high temperatures has long been known. Catalysts suggested for this process include oxides of thorium, zirconium, titanium, calcium, barium, cerium, chromium, aluminum, lanthanum, neodymium, samarium, etc. However, with all of these catalysts, there is a problem with obtaining selective formation of a mixed ketone derived from a mixture of carboxylic acids. Due to the nature of the ketonization reaction, each molecule of ketone is produced from two molecules of carboxylic acids. Consequently, a mixture of two carboxylic acids gives three possible ketone products. Two symmetrical ketones are derived from the same type of carboxylic acid, and the third one, a mixed ketone, is derived from two different carboxylic acids. When the mixed ketone is the desired product, there is a need to increase the selectivity to the mixed ketone, i.e., to produce a smaller amount of the other two symmetrical ketones.

While a number of catalysts have been suggested in the literature for the ketonization, there is little teaching in the art on how to improve the selectivity to the mixed ketone. One such example is given in U.S. Pat. No. 4,950,763. However, the selectivity to the mixed ketone in the '763 patent is close to the statistically expected value. In the current invention, we have discovered certain catalysts that can produce mixed ketones with a selectivity much higher than the statistically expected value.

One factor determining selectivity to the mixed ketone is the molar ratio of the two acids used for its preparation. The theoretical selectivity is based on the assumption that two components, A and B, have equal reactivity and equal probability of forming either a symmetrical or a mixed product. If A and B are present in equal amounts, the probability of forming product M, AB, and BB is 25%, 50%, and 25%, respectively. In general, the probability of forming a mixed product AB from a mixture of A and B can be calculated by trivial formulas, $R/(R+1)$ based on starting material B, and $1/(R+1)$ based on starting material A, where R is the molar ratio of A:B. In the above example, since the amount of A and B is equal, one half of A goes to AA, and another half goes to AB. Thus, the theoretical selectivity to M and AB is 50% each, based on A. Similarly, BB and AB are formed in 50% selectivity based on starting material B.

The '763 patent reported 99% selectivity to the mixed ketone product, such as propiophenone. However, this high selectivity is due to the general difficulty in forming one of the symmetrical products, benzophenone, regardless of the catalyst used. Benzophenone is difficult to make from benzoic acid in the described process, so the only expected product with the phenyl group would be propiophenone.

In the propiophenone example of the '763 patent, the molar ratio of butyric to benzoic acid is 5.88:1. The selectivity to the mixed ketone, propiophenone, is high, 99%, based on benzoic acid, which is above the statistically expected value of 85.5%. As mentioned above, this fact is due to the natural difficulties in making the benzophenone molecule, regardless of the type of catalyst used. However, from the '763 patent, it is not clear what the observed selectivity to propiophenone was, based on the other acid, butyric acid. In any case, the high ratio of butyric to benzoic acid used in this example dictates the theoretically expected selectivity to be 14.5%, which is very low. The reason for spending so much butyric acid is that butyric acid makes dipropyl ketone more readily than the mixed one, propiophenone. Ideally, it would be desirable to have a catalyst that makes only the mixed ketone from a pair of acids, using a 1:1 molar ratio, or at least provides selectivity to the mixed ketone higher than expected statistically on the basis of either acid.

In another example, but one where a symmetrical product can be formed, the '763 patent reported 72% selectivity to the mixed ketone, methyl isopropyl ketone, made from isobutyric acid and acetic acid, on an isobutyric acid basis, at a 1.5:1 molar ratio of acetic acid to isobutyric acid. This selectivity is much lower than the 99% discussed above, but it is better than the theoretical selectivity of 60%. However, the selectivity to the mixed ketone on an acetic acid basis is not reported. Since acetic acid is used in excess to isobutyric acid, it is expected that the symmetrical ketone, in this case acetone, is made in a larger amount than the desired product, methyl isopropyl ketone.

One of the purposes of the current invention, therefore, is to find catalysts that provide high selectivity to a mixed ketone from a mixture of carboxylic acids and that make less of the symmetrical ketones.

SUMMARY OF THE INVENTION

In one aspect, the present invention relates to a catalyst composition comprising zirconium dioxide or a mixture of zirconium dioxide and titanium dioxide, and a salt comprising a cation selected from Groups 1 and 2 of the Periodic Table of Elements and an anion selected from silicate and phosphate.

In another aspect, the invention relates to a process for preparing a mixed ketone, which comprises contacting a mixture of carboxylic acids with the above catalyst composition at conditions effective to produce a mixed ketone.

DETAILED DESCRIPTION OF THE INVENTION

It has been surprisingly discovered that the treatment of zirconia and zirconia-titania catalysts with a Group 1 or 2 metal phosphate or silicate salt can increase selectivity to the desired mixed ketone. As a measure of catalyst performance, deviation from the statistically expected value was chosen. It was surprising that selectivity on the basis of both the more reactive and the less reactive acid can increase after such treatment in a broad range of molar ratios of the more reactive to the less reactive acid.

The catalyst compositions of the invention may be prepared in a number of ways, as will be apparent to persons skilled in the art. One method is by soaking commercially available zirconium dioxide (zirconia) or zirconium dioxide and titanium dioxide (zirconia-titania) in an aqueous solution of a Group 1 or 2 metal phosphate or silicate salt. Potassium or sodium silicate, potassium or sodium phosphate, dipotassium or sodium hydrogen phosphate, or potassium or sodium dihydrogen phosphate can be used as typical salts for the catalyst treatment. But other metals from Groups 1 and 2 of the Periodic Table of Elements may be used to make salts for the catalyst treatment. Although we do not want to be bound by any theories, we believe that the salt treatment is somehow selectively poisoning the metal oxide, so that the reactivity of both acids become more equal, and the catalyst becomes more selective toward the mixed ketone formation.

Other methods can be used to incorporate the salt into the final catalyst composition. For example, a mixture of zirconia and silica may be treated with a caustic (NaOH) to dissolve the silica. After the catalyst is washed with water, and dried, its composition will be close to that of pure zirconia treated with sodium silicate. In a similar way, zirconia phosphate could be treated with a strong caustic to modify its surface groups to resemble zirconia treated with sodium phosphate.

As the active catalyst material, zirconia or zirconia-titania mixture can be used. Both materials may be obtained commercially from vendors such as Saint-Gobain Norpro. The most preferred active catalyst material is a mixture of zirconia and titania. The preferred weight percent of zirconia in the active catalyst material ranges from above 50% to 100%. The more preferred range is from 55% to 95%. The most preferred distribution is around 60% zirconia by weight.

The catalyst composition may include other components that do not adversely affect the reaction, such as inert material. Inert material may include materials with low surface area. The inert material can be premixed with the active catalyst material, or can be added as a mechanically separable material from the catalyst composition when it is loaded into the reactor. The inert material is not counted in the preferred range of zirconia and titania weight distribution. Thus, the catalyst composition may include silica as the major component, for example, 90% by weight, and 4% titania and 6% zirconia. The active components in this case will constitute 40% titania and 60% zirconia by weight according to our definition. We define the inert material as one in which its pure form does not catalyze ketonization of carboxylic acids in greater than 1-5% yield under typical conditions used in our invention.

Commercial active catalyst material is used as an example in the current invention. Alternatively, the active catalyst material may be prepared by precipitation of zirconium or zirconium and titanium oxides from their salts, or by hydrolysis of zirconium or zirconium and titanium alkoxides, as is well known to those skilled in the art. Such precipitation can be done in the presence of the phosphate or silicate salt as a way to incorporate such salts into the catalyst. For example, zirconium nitrate, sulfate, or chloride can be treated with a base in the presence of an aqueous solution of potassium or sodium phosphate or silicate, followed by calcination. In some cases, an aqueous solution of potassium or sodium phosphate or silicate can be used as the base for treating zirconium salts in the described method of catalyst preparation. The degree of salt incorporation in the catalyst can be controlled during the stages of precipitation and the precipitate washing with water.

The surface area of the active catalyst material can range from 1 to 150 $m^2/g$. It can also range from 10 to 100 $m^2/g$ or from 70 to 90 $m^2/g$. For example, the surface area of Catalyst B in Example 1 below is about 86 $m^2/g$.

The degree of catalyst surface coverage with the salt can be between 0.1% and 99% molar. The degree of salt coverage can also be 10-90% or, more particularly, 20-40% molar. For example, if 100 g sample of zirconia active catalyst material with the specific surface area of 100 $m^2/g$ gained 6.0 g weight after treatment with disodium hydrogen phosphate (F.W. 120), its surface would have 50 mmol of disodium hydrogen phosphate, distributed on 100×100=10000 $m^2$, i.e., $5*10^{-6}$ mol/$m^2$. Assuming each Zr atom occupies 0.1-0.15 $nm^2$ of a typical surface of the monoclinic form of zirconia, i.e. $11.1*10^{-6}$-$16.6*10^{-6}$ mol/$m^2$, then $ZrO_2$ surface coverage by disodium hydrogen phosphate in this example is estimated as 30-45%.

After the salt treatment, the catalyst may be dried and/or calcined at elevated temperature. This step is optional since the catalyst will typically be heated in the reactor before it contacts any starting material. During that heating step, the catalyst is effectively dried and/or calcined.

The Group 1 or 2 metal will typically exist on the surface of the treated zirconia or zirconia-titania catalyst as a phosphate or silicate salt. Some of the Group 1 or 2 metal, however, may exist in its oxide or hydroxide form, particularly when excess metal cation is present during the treatment step. Preferably, the total amount of Group 1 or 2 metal (regardless of its form) on the surface of the catalyst ranges from 0.001 to 5%, and more preferably, from 0.1 to 1.5% by weight, based on the total weight of the finished catalyst. For example, the amount of potassium in Catalyst B of Example 1 below is 1.16% by weight.

The catalyst of the present invention contains phosphorus or silicon as part of the phosphate or silicate group, respectively. The amount of phosphorus or silicon on the surface of the catalyst can range from greater than 0 to 0.45%, and more preferably, from 0.001 to 0.010% by weight, based on the total weight of the finished catalyst. For example, the amount of phosphorus on the surface of Catalyst B in Example 1 before is 0.008% by weight. It is to be noted that while the bulk catalyst material may contain phosphorus or silicon within its internal framework, such phosphorus or silicon is not included within this parameter unless it exists as phosphate or silicate, and it appears on the surface of the catalyst.

The catalyst pore size distribution is preferably greater than bi-modal, such as tri-modal.

The catalyst composition of the invention may be used alone as the single catalyst for the mixed ketone production, or may be used in a combination with other catalysts for the optimum production of mixed ketones. The mixture of carboxylic acids can include from 2 to 10 different acids, with 2 to 5 being more preferred, and 2 being the most preferred number.

Carboxylic acids that can be converted to mixed ketones using the catalysts of the present invention include those having the general formulae (Ia) and (Ib):

(Ia)

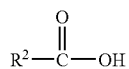

(Ib)

where $R^1$ and $R^2$ are different and are each independently alkyl, cycloalkyl, arylalkyl, aryl, or hetaryl.

The mixed ketones that are produced have the general formula (II):

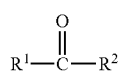

(II)

where $R^1$ and $R^2$ are the same as in formulae (Ia) and (Ib).

$R^1$ and $R^2$ are each preferably alkyl having 1 to 17 carbon atoms, cycloalkyl having 3 to 8 ring members, arylalkyl of 7 to 12 carbon atoms, aryl or hetaryl, and one or more of the radicals $R^1$ and $R^2$ carry one or more hydrogen atoms on the α-carbon atom.

Examples of mixed ketones that are obtainable by the process of the present invention include methyl ethyl ketone, methyl propyl ketone, methyl isopropyl ketone, ethyl isopropyl ketone, acetophenone, propiophenone, butyrophenone, isobutyrophenone, valerophenone, phenylacetone, cyclohexyl methyl ketone, cyclohexyl phenyl ketone, cyclopropyl methyl ketone, pinacolone, and even heterocyclic ketones, such as 3-acetylpyridine, 4-acetylpyrazole, and 4-acetylimidazole.

The carboxylic acids may be brought into contact with the catalyst composition in any reactor known in the art.

The reaction may be carried out at a 50-99% conversion of the less reactive acid, with 60-95% being the most preferred. Complete, or a near complete conversion of the more reactive acid is preferred, although not required in our invention. The molar ratio of the less reactive to the more reactive acid can range from 0.25:1 to 4:1, with 1:1 being the most preferred ratio. Unreacted acids may be recycled. Alternatively, they may be disposed of if their conversion is near completion, e.g., 95-100%.

The temperature and space time velocity for carrying out the reaction may be varied to provide the desired acid conversion rate. Typical temperatures include 300 to 500° C., with 400 to 475° C. being the most preferred range. The space time velocity is calculated as the volume of the liquid feed per volume of the catalyst bed per one hour. The typical space time velocity include the range from 0.25 to 4 $hr^{-1}$, with 1-2 $hr^{-1}$ being the most preferred one.

The ketonization reaction can be run over a wide range of pressures. Suitable pressures include 0 to 800 psi. Preferred pressures include 50 to 100 psi.

It is possible to feed the carboxylic acids into the reactor with up to 50 weight percent of water. Water can prolong catalyst life by preventing coke formation on the catalyst.

When the activity and/or selectivity of the catalyst decrease due to coking, the catalyst is preferably regenerated using a gas containing 0.1-100 percent oxygen at appropriate temperatures for various times, the key being how much carbon dioxide and carbon monoxide exist in the off-gases. A more preferable range is 1-20 percent with the most preferable range being 3-10 percent oxygen. Any inert diluent can be used in the regenerating gas, including nitrogen, helium, argon, neon, and water. It is possible to use carbon dioxide as the oxidant while monitoring the amount of carbon monoxide existing in the off-gases. In this case, the carbon dioxide serves as both the inert diluent and the source of oxygen. And it may be diluted with any other inert diluent. But using carbon dioxide generally requires higher regeneration temperatures.

Regeneration temperatures generally fall in the 300-700° C. range. More preferably, they exist in the 350-600° C. range. And the most preferable temperatures for catalyst regeneration are 400-500° C. At the most preferable regeneration temperatures, the time required to reduce the carbon oxides to 1 percent of their highest level is generally 0.5 to 8 hours with a feed rate of 10 catalyst volumes per hour of the regenerating gas.

This regeneration treatment can remove up to several weight percent of carbon on the catalyst surface. It can also restore essentially complete catalyst activity. The catalyst integrity is unaffected because of the inherent strength of the catalyst material and the fact that the treatment takes place at mild temperatures.

As mentioned above, suitable inert agents to use during the regeneration process include water, nitrogen, carbon dioxide, argon, helium, and neon. The most preferred agents are water and nitrogen solely because they are most readily available and least expensive.

It has been surprisingly discovered that the yield of the mixed ketone can be further improved by combining two types of certain catalyst beds in series.

In the first bed or section of the reactor, the catalyst can be zirconia, anatase form of titania, ceria, oxides of lanthanoids, or mixtures of thereof, treated with a phosphate or a silicate. The form of the phosphate can be monobasic, dibasic, or tribasic phosphates of Group 1 elements. For example, the phosphate compound can be dipotassium hydrogen phosphate, $K_2HPO_4$, or potassium dihydrogen phosphate, $KH_2PO_4$. The preferred phosphate salts are made of potassium or sodium. Organic salts, such as amines, or a free acid, can also be used in this embodiment.

The most preferred catalyst for the first (inlet) section of the reactor is a mixed titania-zirconia catalyst treated with dipotassium hydrogen phosphate as described hereinabove.

The temperature in the first reactor section can be anywhere from 250 to 450° C. The preferred range of temperature in the first section is 300 to 400° C., depending on the mixed ketone and its constituent acids. For methyl ketones made from a mixture of acetic and another acid with a relatively low molecular weight, e.g., 2-5 carbons, the most preferred temperature in the first section is below 425° C. For a more branched, higher molecular weight acid, the upper limit of the first section temperature may be slightly higher, e.g., up to 450° C. The exact temperature needed for the maximum yield may be adjusted to achieve 50-90% conversion of the less reactive acid in the first section of the reactor.

The second section of the reactor can be placed in a higher temperature zone, e.g., from 400 to 525° C. The preferred temperature in the second reactor section is from 450 to 500° C., with the 460 to 480° C. being the most preferred.

The most preferred catalyst for the second section is zirconia treated with KOH. Other catalysts that can be used in this section include the rutile form of titania, other oxides of Group 4, oxides of lanthanoids, such lanthanum oxide, cerium oxide, neodymium oxide, samarium oxide, etc., treated with Group 1 or Group 2 hydroxides, such as KOH, NaOH, etc.

The preferred conversion of the less reactive acid is 50-90% in the first section of the reactor. The preferred overall conversion of both acids in the reactor is close to 100%, although conversions from 50% to 99% can also be used for some less reactive acids. Other parameters, such an hourly space time velocity and the temperature profile in the reactor, can be adjusted to achieve the desired conversion.

As used herein, the indefinite article "a" means one or more.

Unless otherwise indicated, all numbers expressing quantities of ingredients, properties such as molecular weight, reaction conditions, and so forth used in the description and claims are to be understood as being modified in all instances by the term "about." Accordingly, unless indicated to the contrary, the numerical parameters set forth in the following description and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10.

Notwithstanding that the numerical ranges and parameters describing the invention are approximations, the numerical values set forth in the specific examples are reported as precisely as possible. Any numerical value, however, inherently contains certain errors necessarily resulting from the standard deviation found in their respective testing measurements.

The invention is further illustrated and described by the following examples.

EXAMPLES

Active catalyst material, titania, zirconia, and mixed zirconia and titania, were obtained from commercial sources, Engelhard and Saint-Gobain Norpro. Analyses were completed using Varian 6890+ gas chromatograph equipped with a 30 meter Quadrex 007 CW (carbowax) capillary column, 0.53 mm in diameter, and a thermal conductivity detector.

Yield is defined as the ratio of the number of moles of product obtained to the number of moles of the starting material. Conversion is defined as the ratio of the number of moles of starting material reacted to the number of moles of the starting material. Selectivity is defined as the ratio of the number of moles of product obtained to the number of moles of the starting material reacted.

Example 1

Catalyst Preparation

Catalyst A (Comparative)—Mixed Titania-Zirconia Treated with Potassium Hydroxide 100 g of a catalyst material containing 40% titania and 60% zirconia by weight, surface area 86.7 $m^2/g$, were soaked in 100 ml of a 10% solution of KOH in water for 24 hrs at 60° C. under vacuum. The KOH solution was drained; the catalyst was washed with 100 ml of deionized water, three times, and dried at 130° C. for 4 hrs.

Catalyst B—Mixed Titania-Zirconia Treated with Potassium Phosphate 300 g of a catalyst material containing 40% titania and 60% zirconia by weight and having surface area 86.7 $m^2/g$ were soaked in 300 ml of an aqueous solution containing 13.2 g of KOH (0.236 mol) and 11.5 g of $H_3PO_4$ (0.117 mol), for 12 hrs at room temperature. The solution was drained; the catalyst was washed once with deionized water, 100 ml, and dried under vacuum at 70° C. for 24 hrs. The catalyst gained 6.9 g of $K_2HPO_4$. Estimated surface coverage is 9.2-13.7%.

Catalyst C (Comparative)—Zirconia Treated with Potassium Hydroxide 100 g of zirconia with a 52 $m^2/g$ surface area were soaked in 100 ml of a 10% solution of KOH in water for 24 hrs at 60° C. under vacuum. The KOH solution was drained; the catalyst was washed with 100 ml of deionized water, three times, and dried at 130° C. for 4 hrs.

Catalyst D (Comparative)—Titania Treated with Potassium Hydroxide

Same as in Catalyst C, except titania with a 48 $m^2/g$ surface area was used as the catalyst material.

Catalyst E—Zirconia Treated with Potassium Silicate

Same as in Catalyst C, except a 10% solution of $K_2SiO_3$ was used.

Catalyst F—Zirconia Treated with Sodium Silicate

Same as in Catalyst C, except a 10% solution of $Na_2SiO_3$ was used.

Catalyst G—Zirconia Treated with Potassium Phosphate 100 g of zirconia with a 48 $m^2/g$ surface area, were soaked in 100 ml of an aqueous solution containing 4.4 g KOH (0.078 mol) and 4.5 g $NH_4H_2PO_4$ (0.039 mol) for 96 hrs at RT under vacuum. The solution was drained; the catalyst was washed with 100 ml of deionized water, three times, dried at 130° C. for 2 hrs, and calcined at 450° C. for 2 hrs. The catalyst gained 2.4 g of $K_2HPO_4$. Estimated surface coverage is 17.3-25.9%.

Catalyst H—Mixed Titania-Zirconia Treated with Potassium Phosphate 100 g of a catalyst material containing 40% titania and 60% zirconia by weight were soaked in a 100 ml aqueous solution containing 4.1 g $K_3PO_4$ (19.5 mmol) for 72 hrs at RT under vacuum. The $K_3PO_4$ solution was drained; the catalyst was washed with 100 ml of deionized water, three times, dried at 130° C. for 2 hrs, and calcined at 450° C. for 2 hrs. The catalyst gained 2.6 g of $K_3PO_4$. Estimated surface coverage is 15.4-23.1%.

Catalyst I (Comparative)—Untreated Zirconia

Untreated zirconia in the form of cylinders, 25×25 mm size, was used from a commercial source as is, without doing any modification to it. The catalyst surface area was 52 $m^2/g$.

Catalyst J (Comparative)—Untreated Titania

Untreated titania in the form of cylinders, 25×25 mm size, was used from a commercial source as is, without doing any modification to it. The catalyst surface area was 48 $m^2/g$.

Catalyst K (Comparative)—Untreated Mixed Titania-Zirconia

Commercial catalyst, 40% titania and 60% zirconia by weight, surface area 86.7 $m^2/g$, was used as is, without any modification of its properties.

Example 2

Methyl Isopropyl Ketone Preparation

For each of the runs reported in Table 1 below, 70 ml of a particular catalyst from Example 1 were placed in a stainless steel reactor, one inch in diameter. The bottom and the top of the catalyst bed were each filled with 10 ml of glass beads. The reactor was heated inside an electric furnace to a temperature indicated in Table 1. A mixture of acetic and isobutyric acid in three different molar ratios, 0.25:1, 1:1, and 1.6:1, having 10% water by weight, was introduced from the top to the bottom of the reactor through a line preheated to 170° C. at the rate of 70 ml/hr. The reaction was conducted at atmospheric pressure. The product was collected every 1-2 hrs in a condenser chilled to 0° C., weighed, and analyzed by GC. The results are summarized in the Table 1.

TABLE 1

Preparation of MIPK from acetic and isobutyric acid.

| Run | Catalyst | Acid Molar Ratio | Temp., °C. | Space time velocity, hr −1 | Isobutyric Acid Conversion, % | MIPK Yield on Isobutyric Acid Basis, % | MIPK Selectivity on Isobutyric Acid Basis, % | Acetic Acid Conversion |
|---|---|---|---|---|---|---|---|---|
| 1 | $TiO_2/ZrO_2/K_2HPO_4$ | 0.25 | 425 | 2 | 29.7 | 18.6 | 62.7 | 91.5 |
| 2 | $ZrO_2/K_2SiO_3$ | 0.25 | 425 | 2 | 66.7 | 20.5 | 30.3 | 99.1 |
| 3 | $ZrO_2$ | 0.25 | 425 | 2 | 55.4 | 18.9 | 33.7 | 97.9 |
| 4 | $TiO_2$ | 0.25 | 425 | 2 | 43.5 | 15.5 | 35.0 | 90.5 |
| 5 | $TiO_2/ZrO_2/KOH$ | 0.25 | 425 | 2 | 43.8 | 17.2 | 38.6 | 100.0 |
| 6 | $TiO_2/KOH$ | 0.25 | 425 | 2 | 52.4 | 17.7 | 33.4 | 99.0 |
| 7 | $ZrO_2/KOH$ | 0.25 | 425 | 2 | 71.4 | 16.9 | 23.3 | 99.4 |
| 8 | $TiO_2/ZrO_2/K_2HPO_4$ | 1.0 | 375 | 1 | 33.4 | 28.0 | 83.8 | 65.6 |
| 9 | $TiO_2/ZrO_2/K_2HPO_4$ | 1.0 | 475 | 4 | 59.5 | 49.9 | 82.6 | 91.7 |
| 10 | $TiO_2/ZrO_2/KOH$ | 1.0 | 375 | 1 | 38.8 | 38.8 | 100.0 | 96.6 |
| 11 | $TiO_2/ZrO_2/KOH$ | 1.0 | 475 | 4 | 61.1 | 50.9 | 82.0 | 97.5 |
| 12 | $TiO_2/KOH$ | 1.0 | 425 | 2 | 78.4 | 49.8 | 62.8 | 99.5 |
| 13 | $TiO_2/KOH$ | 1.0 | 525 | 2 | 98.1 | 50.2 | 51.2 | 99.8 |
| 14 | $ZrO_2/KOH$ | 1.0 | 425 | 0.5 | 91.9 | 52.7 | 57.3 | 99.8 |
| 15 | $ZrO_2/KOH$ | 1.0 | 425 | 2 | 80.3 | 40.4 | 49.8 | 99.8 |
| 16 | $ZrO_2/KOH$ | 1.0 | 525 | 2 | 99.7 | 37.6 | 37.7 | 99.9 |
| 17 | $TiO_2$ | 1.0 | 425 | 0.5 | 66.2 | 53.3 | 80.5 | 93.3 |
| 18 | $TiO_2$ | 1.0 | 525 | 2 | 84.3 | 38.0 | 44.6 | 98.0 |
| 19 | $ZiO_2$ | 1.0 | 425 | 0.5 | 98.2 | 46.5 | 47.4 | 99.9 |
| 20 | $ZrO_2$ | 1.0 | 525 | 2 | 95.0 | 29.2 | 30.5 | 98.8 |
| 21 | $TiO_2/ZrO_2/K_2HPO_4$ | 1.6 | 425 | 0.5 | 93.8 | 81.3 | 86.4 | 99.5 |
| 22 | $TiO_2/ZrO_2/K_2HPO_4$ | 1.6 | 450 | 1 | 91.1 | 78.3 | 85.9 | 98.6 |
| 23 | $TiO_2/ZrO_2/K_2HPO_4$ | 1.6 | 475 | 1 | 97.5 | 75.6 | 77.6 | 99.4 |
| 24 | $TiO_2/ZrO_2/K_2HPO_4$ | 1.6 | 425 | 2 | 58.1 | 55.4 | 95.3 | 85.5 |
| 25 | $TiO_2/ZrO_2/K_2HPO_4$ | 1.6 | 475 | 2 | 87.6 | 71.4 | 81.5 | 99.0 |
| 26 | $TiO_2/ZrO_2/K_2HPO_4$ | 1.6 | 525 | 2 | 97.7 | 68.8 | 70.3 | 99.9 |
| 27 | $TiO_2/ZrO_2/K_3PO_4$ | 1.6 | 475 | 1 | 98.8 | 76.1 | 77.0 | 99.8 |
| 28 | $TiO_2/ZrO_2/K_3PO_4$ | 1.6 | 475 | 2 | 87.5 | 71.4 | 81.6 | 99.6 |
| 29 | $TiO_2/ZrO_2/KOH$ | 1.6 | 425 | 0.5 | 99.8 | 78.7 | 78.9 | 100.0 |
| 30 | $TiO_2/ZrO_2/KOH$ | 1.6 | 425 | 2 | 77.0 | 62.5 | 80.2 | 99.5 |
| 31 | $TiO_2/ZrO_2/KOH$ | 1.6 | 525 | 2 | 99.4 | 66.1 | 66.4 | 99.9 |
| 32 | $TiO_2/KOH$ | 1.6 | 475 | 1 | 99.0 | 69.9 | 70.5 | 99.8 |
| 33 | $TiO_2/KOH$ | 1.6 | 475 | 4 | 80.9 | 57.9 | 70.7 | 98.9 |
| 34 | $TiO_2/KOH$ | 1.6 | 475 | 1 | 94.7 | 65.7 | 69.2 | 97.7 |
| 35 | $ZrO_2/K_2HPO_4$ | 1.6 | 475 | 1 | 88.1 | 61.0 | 69.2 | 99.8 |
| 36 | $ZrO_2/K_2HPO_4$ | 1.6 | 475 | 2 | 54.4 | 47.3 | 87.0 | 90.0 |
| 37 | $ZrO_2/K_2SiO_3$ | 1.6 | 475 | 1 | 88.1 | 65.5 | 73.9 | 97.4 |
| 38 | $ZrO_2/Na_2SiO_3$ | 1.6 | 475 | 1 | 92.0 | 63.8 | 69.1 | 98.6 |
| 39 | $ZrO_2$ | 1.6 | 475 | 1 | 88.6 | 45.2 | 50.6 | 98.5 |
| 40 | $TiO_2/ZrO_2$ | 1.6 | 450 | 1 | 83.2 | 53.0 | 62.5 | 93.2 |
| 41 | $TiO_2$ | 1.6 | 475 | 1 | 95.7 | 22.2 | 23.2 | 88.3 |

| Run | MIPK Yield on Acetic Acid Basis, % | MIPK Selectivity on Acetic Acid Basis, % | Statistically Expected Selectivity on Isobutyric Acid Basis, % | Statistically Expected Selectivity on Acetic Acid Basis, % | Deviation from the Statistically Expected Selectivity, on Isobutyric Acid Basis, % | Deviation from the Statistically Expected Selectivity, on Acetic Acid Basis, % | Sum of Deviations, % |
|---|---|---|---|---|---|---|---|
| 1 | 72.5 | 79.2 | 20 | 80 | 42.7 | −0.8 | 41.9 |
| 2 | 81.8 | 82.5 | 20 | 80 | 10.3 | 2.5 | 12.9 |
| 3 | 75.7 | 77.3 | 20 | 80 | 13.7 | −2.7 | 11.1 |
| 4 | 62.1 | 68.6 | 20 | 80 | 15.0 | −11.4 | 3.6 |
| 5 | 66.9 | 66.9 | 20 | 80 | 18.6 | −13.1 | 5.5 |
| 6 | 70.8 | 71.5 | 20 | 80 | 13.4 | −8.5 | 4.9 |
| 7 | 67.5 | 67.9 | 20 | 80 | 3.3 | −12.1 | −8.9 |
| 8 | 27.1 | 41.3 | 50 | 50 | 33.8 | −8.7 | 25.1 |
| 9 | 48.3 | 52.7 | 50 | 50 | 32.6 | 2.7 | 35.3 |
| 10 | 38.3 | 39.7 | 50 | 50 | 50.0 | −10.3 | 39.7 |
| 11 | 49.3 | 50.6 | 50 | 50 | 32.0 | 0.6 | 32.5 |
| 12 | 49.8 | 50.0 | 50 | 50 | 12.8 | 0.0 | 12.8 |
| 13 | 50.2 | 50.3 | 50 | 50 | 1.2 | 0.3 | 1.5 |

TABLE 1-continued

Preparation of MIPK from acetic and isobutyric acid.

| | | | | | | | |
|---|---|---|---|---|---|---|---|
| 14 | 52.7 | 52.8 | 50 | 50 | 7.3 | 2.8 | 10.1 |
| 15 | 40.3 | 40.4 | 50 | 50 | −0.2 | −9.6 | −9.8 |
| 16 | 37.6 | 37.6 | 50 | 50 | −12.3 | −12.4 | −24.7 |
| 17 | 53.2 | 57.0 | 50 | 50 | 30.5 | 7.0 | 37.5 |
| 18 | 38.0 | 38.8 | 50 | 50 | −5.4 | −11.2 | −16.6 |
| 19 | 46.5 | 46.5 | 50 | 50 | −2.6 | −3.5 | −6.1 |
| 20 | 29.2 | 29.5 | 50 | 50 | −19.5 | −20.5 | −40.0 |
| 21 | 50.4 | 50.6 | 62 | 38 | 24.7 | 12.4 | 37.0 |
| 22 | 48.9 | 49.6 | 62 | 38 | 24.2 | 11.3 | 35.6 |
| 23 | 47.2 | 47.5 | 62 | 38 | 15.8 | 9.2 | 25.1 |
| 24 | 34.3 | 40.2 | 62 | 38 | 33.6 | 1.9 | 35.5 |
| 25 | 44.6 | 45.1 | 62 | 38 | 19.8 | 6.8 | 28.8 |
| 26 | 42.7 | 42.7 | 62 | 38 | 8.6 | 4.4 | 13.0 |
| 27 | 47.5 | 47.6 | 62 | 38 | 15.2 | 9.3 | 24.6 |
| 28 | 44.6 | 44.8 | 62 | 38 | 19.9 | 6.5 | 26.4 |
| 29 | 48.8 | 48.8 | 62 | 38 | 17.2 | 10.5 | 27.7 |
| 30 | 38.7 | 38.9 | 62 | 38 | 18.4 | 0.6 | 19.1 |
| 31 | 41.0 | 41.0 | 62 | 38 | 4.7 | 2.7 | 7.4 |
| 32 | 43.6 | 43.7 | 62 | 38 | 8.9 | 5.3 | 14.2 |
| 33 | 36.2 | 36.6 | 62 | 38 | 9.1 | −1.8 | 7.3 |
| 34 | 41.1 | 42.0 | 62 | 38 | 7.6 | 3.6 | 11.2 |
| 35 | 38.1 | 38.2 | 62 | 38 | 7.6 | −0.2 | 7.4 |
| 36 | 29.5 | 32.8 | 62 | 38 | 25.4 | −5.6 | 19.8 |
| 37 | 40.9 | 42.0 | 62 | 38 | 12.3 | 3.6 | 15.9 |
| 38 | 39.8 | 40.4 | 62 | 38 | 7.5 | 2.0 | 9.5 |
| 39 | 28.2 | 28.6 | 62 | 38 | −11.0 | −9.8 | −20.8 |
| 40 | 33.1 | 35.5 | 62 | 38 | 0.9 | −2.9 | −2.0 |
| 41 | 13.9 | 15.7 | 62 | 38 | −38.4 | −22.7 | −61.1 |

Selectivity values above the statistically expected ones are shown in bold.

Normally, the selectivity to the mixed ketone on the basis of the more reactive acid is below the statistically expected value because the more reactive acid tends to react with itself, rather than with another, less reactive acid. In the examples shown in Table 1, acetic acid is more reactive and makes more acetone than MIPK. The deviation of the MIPK selectivity on the acetic acid basis is negative for many comparative catalysts, $ZrO_2$, $TiO_2$, $ZrO_2/KOH$, $TiO_2/KOH$ (see Runs 3-4, 6-7, 12-20, 33, and 39-41 in Table 1). Surprisingly, for $ZrO_2$, and especially for the mixture of $ZrO_2$ and $TiO_2$, phosphate or silicate treatment is a very useful method for improving the selectivity to the mixed ketone, MIPK (see Runs 2, 9, 21-28, and 37-38 in Table 1). The selectivity on the basis of both acetic and isobutyric acid is above expectation for $ZrO_2$ and $ZrO_2/TiO_2$ treated with phosphate or silicate. With the catalysts discovered in our invention, mixed ketones can be produced in a more economical way, since a smaller amount of both carboxylic acids are spent for their production.

Example 3

Preparation of Methyl Isobutyl Ketone (MIBK)

Example 2 was repeated with Catalyst B from Example 1, except a mixture of acetic and isovaleric acid in molar ratio of 1:1, having 10% water by weight, was introduced from the top to the bottom of the reactor through a line preheated to 170° C. at the rate of 70 ml/hr. The reaction was conducted at atmospheric pressure. The product was collected every 1-2 hrs in a condenser chilled to 0° C., weighed, and analyzed by GC. This experiment was run two times at different temperatures. The results are summarized in the Table 2 below.

Example 4

Comparative

Example 3 was repeated, except Catalyst A from Example 1 was used. This experiment was run two times. The results are summarized in Table 2 below.

TABLE 2

Comparison of catalyst performance for MIBK production.

| | | | | | Isovaleric acid basis | | | |
|---|---|---|---|---|---|---|---|---|
| Example No. | Run | Catalyst | Top Temp. (° C.) | Bottom Temp. (° C.) | Conversion, % | MIBK Yield, % | MIBK Selectivity, % | Acetic acid basis Conversion, % |
| 6 | A | $TiO_2/ZrO_2/K_2HPO_4$ | 400 | 450 | 73.8 | 36.5 | 49.4 | 99.2 |
| 6 | B | $TiO_2/ZrO_2/K_2HPO_4$ | 430 | 475 | 93.8 | 36.9 | 39.3 | 99.8 |

TABLE 2-continued

Comparison of catalyst performance for MIPK production.

| | | | | | | | |
|---|---|---|---|---|---|---|---|
| 7 | C | TiO$_2$/ZrO$_2$/KOH | 400 | 450 | 87.6 | 31.5 | 35.9 | 100.0 |
| 7 | D | TiO$_2$/ZrO$_2$/KOH | 420 | 475 | 98.8 | 34.7 | 35.2 | 100.0 |

| | | Acetic acid basis | | | | | GC Accountability | |
|---|---|---|---|---|---|---|---|---|
| Example No. | Run | MIBK Yield, % | MIBK Selectivity, % | Acetone Yield, % | Acetone Selectivity, % | Mass Balance % | Organic Phase % | Aqueous Phase % |
| 6 | A | 36.5 | 36.8 | 51.1 | 51.6 | 100.1% | 99.8 | 99.3 |
| 6 | B | 36.9 | 36.9 | 45.1 | 45.2 | 99.0% | 97.1 | 99.9 |
| 7 | C | 31.5 | 31.5 | 53.7 | 53.7 | 100.0% | 98.1 | 99.8 |
| 7 | D | 34.7 | 34.7 | 42.5 | 42.5 | 96.1% | 99.2 | 99.9 |

As seen from Table 2, at the same reaction temperature, MIBK yield and selectivity can be increased, on both isovaleric and acetic acid bases, by using a catalyst treated with phosphate instead of potassium hydroxide. See runs A and C. And while the top reactor temperature in Run B was higher than that in Run D, there is still an improvement in the MIBK yield and selectivity on both acid bases by using a mixed titania-zirconia catalyst treated with potassium phosphate instead of potassium hydroxide.

Example 5

MIPK Preparation with Two Catalyst Beds

The first catalyst, dipotassium hydrogen phosphate treated mixture of zirconium and titanium oxides, 125 ml, was placed in a top section of a stainless steel reactor, one inch in diameter. The second catalyst, 125 ml of KOH treated zirconia was placed in a bottom section of the reactor, right after the first catalyst bed. Glass beads, 10 ml, were placed at the bottom and at the top of the catalyst beds. The reactor was heated inside an electric furnace.

A mixture of acetic and isobutyric acids in a molar ratio 1.9:1, having 10% water by weight, was introduced from the top to the bottom of the reactor through a line preheated to 170° C. at the rate 250 ml/hr. The product was collected every hour in a condenser chilled to 0° C., weighed, and analyzed by GC. Results are summarized in Table 3 below.

Example 6

Comparative—MIPK Preparation with KOH Treated Zirconia Catalyst

Example 5 was repeated, except just one bed of 250 ml of KOH treated zirconia was used. Results are summarized in the Table 3 below.

Example 7

Comparative—MIPK Preparation with K$_2$HPO$_4$ Treated Mixed Zirconia/Titania Catalyst Example 5 was repeated, except just one bed of 250 ml of phosphate treated mixed zirconia and titania catalyst was used. Results are summarized in the Table 3 below.

TABLE 3

MIPK yield based on isobutyric and acetic acids with different catalysts.

| Example # | Catalyst(s) | Isobutyric Acid Conversion (%) | MIPK Yield based on Isobutyric Acid (%) | MIPK Yield based on Acetic Acid (%) | Space Time Velocity (hr$^{-1}$) | Temperature in the Reactor Outlet (° C.) |
|---|---|---|---|---|---|---|
| 5 | TiO$_2$—ZrO$_2$—K$_2$HPO$_4$ and ZrO$_2$—KOH | 98.8 | 82.4 | 43.3 | 2.15 | 474 |
| 6 | ZrO$_2$—KOH | 99.9 | 68.7 | 36.1 | 2.05 | 487 |
| 7 | TiO$_2$—ZrO$_2$—K$_2$HPO$_4$ | 85.7 | 76.2 | 40.1 | 1.21 | 464 |

The invention has been described in detail with particular reference to preferred embodiments thereof, but it will be understood that variations and modifications can be effected within the spirit and scope of the invention.

We Claim:

1. A process for preparing a mixed ketone, said process comprising the step of contacting a mixture of carboxylic acids with a catalyst composition comprising (a) zirconium dioxide and (b) a salt comprising a cation selected from Groups 1 and 2 of the Periodic Table of Elements and an anion selected from silicate and phosphate at conditions effective to produce a mixed ketone, wherein the zirconium dioxide of the catalyst composition has a surface area of 1 to 150 m$^2$/g, and wherein 10 to 90% of the surface area of the zirconium dioxide is covered with the salt.

2. The process according to claim 1, wherein said mixture of carboxylic acids comprises acetic acid and isobutyric acid, and said mixed ketone is methyl isopropyl ketone.

3. The process according to claim 1, wherein said mixture of carboxylic acids comprises a more reactive carboxylic acid and a less reactive carboxylic acid.

4. The process according to claim 3, wherein 50 to 99 percent of the less reactive carboxylic acid is converted.

5. The process according to claim 3, wherein 60 to 95 percent of the less reactive carboxylic acid is converted.

6. The process according to claim 3, wherein the molar ratio of the less reactive carboxylic acid to the more reactive carboxylic acid is 0.25:1 to 4:1.

7. The process according to claim 3, wherein the molar ratio of the less reactive carboxylic acid to the more reactive carboxylic acid is 1:1.

8. The process according to claim 1, wherein any unreacted carboxylic acid is recycled.

9. The process according to claim 1, wherein the zirconium dioxide has a surface area of 70 to 90 $m^2/g$.

10. The process according to claim 9, wherein 20 to 40% of the surface area of the zirconium dioxide is covered with the salt.

11. The process according to claim 1, wherein the cation is sodium or potassium.

12. The process according to claim 1, wherein said catalyst composition further comprises a solid support.

13. The process according to claim 12, wherein the solid support is silica.

14. A process for preparing a mixed ketone, said process comprising the step of contacting a mixture of carboxylic acids with a catalyst composition comprising (a) a mixture of zirconium dioxide and titanium dioxide, and (b) a salt comprising a cation selected from Groups 1 and 2 of the Periodic Table of Elements and an anion selected from silicate and phosphate at conditions effective to produce a mixed ketone, wherein the mixture of zirconium dioxide and titanium dioxide of the catalyst composition has a surface area of 1 to 150 $m^2/g$, and wherein 10 to 90% of the surface area of the mixture of zirconium dioxide and titanium dioxide is covered with the salt.

15. The process according to claim 14, wherein said mixture of carboxylic acids comprises acetic acid and isobutyric acid, and said mixed ketone is methyl isopropyl ketone.

16. The process according to claim 14, wherein said mixture of carboxylic acids comprises a more reactive carboxylic acid and a less reactive carboxylic acid.

17. The process according to claim 16, wherein 50 to 99 percent of the less reactive carboxylic acid is converted.

18. The process according to claim 16, wherein 60 to 95 percent of the less reactive carboxylic acid is converted.

19. The process according to claim 16, wherein the molar ratio of the less reactive carboxylic acid to the more reactive carboxylic acid is 0.25:1 to 4:1.

20. The process according to claim 16, wherein the molar ratio of the less reactive carboxylic acid to the more reactive carboxylic acid is 1:1.

21. The process according to claim 14, wherein any unreacted carboxylic acid is recycled.

22. The process according to claim 14, wherein said mixture of zirconium dioxide and titanium dioxide comprises 55 to 85 weight percent of zirconium dioxide.

23. The process according to claim 14, wherein the mixture of zirconium dioxide and titanium dioxide has a surface area of 70 to 90 $m^2/g$.

24. The process according to claim 23, wherein 20 to 40% of the surface area of the mixture of zirconium dioxide and titanium dioxide is covered with the salt.

25. The process according to claim 14, wherein the cation is sodium or potassium.

26. The process according to claim 14, wherein the catalyst composition further comprises a solid support.

27. The process according to claim 26, wherein the solid support is silica.

* * * * *